US011602510B2

(12) United States Patent
Haghikia (10) Patent No.: US 11,602,510 B2
(45) Date of Patent: Mar. 14, 2023

(54) AGENT FOR USE IN THE TREATMENT OF DYSLIPIDEMIA

(71) Applicant: Flexopharm Brain GMBH & Co. KG, Herne (DE)

(72) Inventor: Aiden Haghikia, Bochum (DE)

(73) Assignee: Flexopharm Brain GMBH & Co. KG, Herne (DE)

( * ) Notice: Subject to any disclaimer, the term of this patent is extended or adjusted under 35 U.S.C. 154(b) by 0 days.

(21) Appl. No.: 16/491,739

(22) PCT Filed: Mar. 9, 2018

(86) PCT No.: PCT/EP2018/055876
§ 371 (c)(1),
(2) Date: Sep. 6, 2019

(87) PCT Pub. No.: WO2018/162698
PCT Pub. Date: Sep. 13, 2018

(65) Prior Publication Data
US 2020/0030267 A1   Jan. 30, 2020

(30) Foreign Application Priority Data
Mar. 9, 2017  (DE) .................... 10 2017 105 036.1

(51) Int. Cl.
*A61K 31/19* (2006.01)
*A61P 3/06* (2006.01)
*A61K 31/40* (2006.01)

(52) U.S. Cl.
CPC .............. *A61K 31/19* (2013.01); *A61K 31/40* (2013.01); *A61P 3/06* (2018.01)

(58) Field of Classification Search
CPC .................................. A61K 31/19; A61P 3/06
See application file for complete search history.

(56) References Cited

U.S. PATENT DOCUMENTS

| 10,226,443 | B2 | 3/2019 | Scher et al. | |
|---|---|---|---|---|
| 2003/0203004 | A1* | 10/2003 | Kelm ........................ | A23L 2/66 424/439 |
| 2007/0248662 | A1 | 10/2007 | Joshi et al. | |
| 2011/0033946 | A1 | 2/2011 | Berenson et al. | |
| 2011/0112010 | A1 | 5/2011 | Hallett et al. | |
| 2017/0231933 | A1 | 8/2017 | Gold et al. | |
| 2018/0214399 | A1 | 8/2018 | Spector et al. | |
| 2018/0303778 | A1 | 10/2018 | Gold et al. | |

FOREIGN PATENT DOCUMENTS

| DE | 19503598 A1 | 8/1996 |
|---|---|---|
| FR | 2782608 A1 | 3/2000 |
| WO | 2010105112 A1 | 9/2010 |
| WO | 2017067681 A1 | 4/2017 |
| WO | 2018162698 A1 | 9/2018 |

OTHER PUBLICATIONS

Jones et al. Am. J. Cardiovasc. Drugs, 2010, vol. 10, No. 2, pp. 73-84 (Year: 2010).*
Lipitor® Prescribing Information (Pfizer, Feb. 2012, 24 pages) (Year: 2012).*
Wägner et al. J. Clin. Endocrinol. Metab., 2003, vol. 88, pp. 3212-3217 (Year: 2003).*
Stojakovic et al. Atherosclerosis, 2010, vol. 209, pp. 178-183 (Year: 2010).*
Thacker et al. Can. J. Animal Sci., Jun. 1982, vol. 62, pp. 527-536 (Year: 1982).*
Sampson TR et al., "Gut microbiota regulate motor deficits and neuroinflammation in a model of Parkinson's disease" Cells 2016, vol. 167, pp. 1469-1480.
St. Laurent R et al., "Sodium butyrate improves locomotor impairment and early mortality in a rotenone-Induced drosophila model of Parkinson's disease" Neuroscience 2013, vol. 246, pp. 382-390.
Lei E et al., "Fatty acids and their therapeutic potential in neurological disorders" Neurochemistry International 2016, vol. 95, pp. 75-84.
Non-Final Office Action for U.S. Appl. No. 16/627,688, filed Apr. 14, 2021.
Canani RB et al., "Potential beneficial effects of butyrate in intestinal and extraintestinal diseases" World J. Gastroenterol. 2011, vol. 17, No. 12, pp. 1519-1528.
Neesby TE "Neesby Butyrex (Butyric Acid, Butyrate) A Calcium Magnesium Butyrate Complex 600 mg 250 capsules" amazon.com, product first available date Oct. 2016. Downloaded from <https://www.amazon.com/Butyrex-Butyric-Butyrate-Magnesium-capsules/dp/B003JOJ04G/ref=sr_1_2?crid=1QWRMHKQDM2GQ&dchild=1&keywords%E2%80%A6>.
ClinicalTrials.gov, NCT02976688, last update posted Nov. 29, 2016.
Armstrong MJ et al., "Diagnosis and treatment of Parkinson disease" JAMA 2020, vol. 323, No. 6, pp. 548-560.
Sigma-Aldrich Catalog "Sodium propionate" Catalog # P5436, retreived from Internet on Apr. 8, 2021. Downloaded from URL: <https://www.sigmaaldrich.com/catalog/product/sigma/p1880?lang=en&region=US>.
Unger MM., "Short chain fatty acids and gut microbiota differ between patients with Parkinson's disease and age-matched controls" Parkinsonism and Related Disorders 2016, vol. 32, pp. 66-72.
The Good Scents Company "ethyl 2-methyl butyrate" Apr. 3, 2016, retrieved from Internet on Apr. 9, 2021. Downloaded from URL: https://web.archive.org/web/20160403214807/http://www.thegoodscentscompany.com/data/rw1004871.html.
Dajose L "Parkinson's Disease Linked to Microbiome" Caltech, Dec. 1, 2016. Retrieved from the internet; URL: <https://www.caltech.edu/about/news/parkinsons-disease-linked-microbiome-53109>.
Bourassa MW, et al. Butyrate, Neuroepigenetics and the Gut Microbiome: Can a High Fiber Diet Improve Brain Health? Neuroscience Letters 2016, vol. 625, pp. 56-63.
Duscha A, et al. "Beneficial Effects of Short Chain Fatty Acids on the Course of Experimental Autoimmune Encephalomyelitis" Journal of Neuroimmunology, Oct. 15, 2014, vol. 275, No. 1 , p. 59 Abstract.

(Continued)

*Primary Examiner* — James D. Anderson
(74) *Attorney, Agent, or Firm* — Wuersch & Gering LLP (57) ABSTRACT

The invention relates to an agent for use in the prophylaxis or treatment of dyslipidemia, in particular for the treatment of excessive/elevated LDL levels, containing propionic acid or a physiologically acceptable propionic acid derivative.

28 Claims, 9 Drawing Sheets

(56) References Cited

OTHER PUBLICATIONS

Smith PM, et al. "The Microbial Metabolites, Short Chain Fatty Acids, Regulate Colonic Treg Cell Homeostasis" Science, Aug. 2, 2013, vol. 341, No. 6145, pp. 569-573.
Haghikia A, et al. "Impact of Fatty Acids on CNS Autoimmunity and Their Therapeutic Potential for Multiple Sclerosis" ECTRIMS Online Library, Oct. 7, 2015. Retrieved from the Internet; URL: http://citenpl.internal.epo.org/wf/web/citenpl/citenpl.html [Retrieved on May 17, 2017] abstract.
Furusawa Y, et al. "Commensal Microbe-Derived Butyrate Induces the Differentiation of Colonic Regulatory T Cells" Nature, Dec. 19, 2013, vol. 504, No. 7480, pp. 446-450.
Berg J, et al. "Beneficial Effects of Short Chain Fatty Acids on the Course of Experimental Autoimmune Encaphalomyelitis" Journal of Neuroimmunology Oct. 15, 2014, vol. 275, No. 1, p. 59.
Gross CC, et al. "Dimethyl Fumarate Treatment Alters Circulating T Helper Cell Subsets in Multiple Sclerosis" Neurology—Neruoimmunology NeuroInflammation, Dec. 10, 2015, vol. 3, No. 1, pp. e183, XP055312762.
Haghikia A, et al. "Session 042—MS and CNS Inflammatory Disease: Risk Factors in Multiple Sclerosis: Therapeutic Potential of Propionic Acid" AAN Meeting 2016, Apr. 16, 2016, pp. 1-1, XP055312758.
International Search report forms 210 and 237 (German and machine translation English) for PCT/EP2015/074179 dated Dec. 2, 2016.
Miller et al., "Clinical Pharmacology of Sodium Butyrate in Patients with Acute Leukemia," European Journal of Cancer and Clinical Oncology 1987, vol. 23, No. 9, pp. 1283-1287 (Abstract).
Lucas S, et al. "Short-Chain Fatty Acids Regulate Systemic Bone Mass and Protect from Pathological Bone Loss" Nature Communications 2018, vol. 9:55, DOI: 10.1038/s41467-017-02490-4 | www.nature.com/naturecommunications.
Berggren AM, et al. "Influence of Orally and Rectally Administered Propionate on Cholesterol and Glucose Metabolism in Obese Rats" British Journal of Nutrition 1996, vol. 76, pp. 287-294.
Venter CS, et al. "Effects of Dietary Propionate on Carbohydrate and Lipid Metabolism in Healthy" The American Journal of Gastroenterology May 1990, vol. 85, No. 5, pp. 549-553 (Abstract).
Lin BY, et al. "Differences in Propionate-Induced Inhibition of Cholesterol and Triacylglycerol Synthesis Between Human and Rat Hepatocytes in Primary Culture" British Journal of Nutrition 1995, vol. 74, pp. 197-207.
Davidson MH, et al. "Efficacy and Tolerability of Atorvastatin/Fenofibrate Fixed-Dose Combination Tablet Compared With Atorvastatin and Fenofibrate Monotherapies in Patients with Dyslipidemia: A 12-Week, Multic-Center, Double-Blind, Randomized, Parallel-Group Study" Clinical Therapeutics 2009, vol. 31, No. 12, paged 2824-2838.
Haghikia A, et al. "Propionate Attenuates Atherosclerosis by Immune-Dependent Regulation of Intestinal Cholesterol Metabolism" European Heart Journal 2022, 43, 518-533, https://doi.org/10.1093/eurheartj/ehab644.
Osto E "The Promise of the Gut Metabolite Propionate for a Novel and Personalized Lipid-Lowering Treatment" European Heart Journal 2022, 43, 534-537, https://doi.org/10.1093/eurheartj/ehab723.

* cited by examiner

AGENT FOR USE IN THE TREATMENT OF DYSLIPIDEMIA

The invention relates to an agent for use in the prophylaxis or therapy of hypercholesterolemia and in particular for the treatment of elevated LDL levels.

Cholesterol is a vital sterol that is synthesized in the human body in an amount of up to 2 g per day. Moreover, cholesterol is also ingested with food. The endogenous cholesterol synthesis has largely been decoded.

Viewed physiologically, cholesterol is an important component of the plasma membrane. It increases the membrane's stability and, together with proteins, makes a contribution to the introduction of signaling substances into and their transfer out of the cell membrane. The human body contains approx. 140 g of cholesterol, with more than 95% of it being found inside cells and cell membranes.

Cholesterol itself is fat-soluble and insoluble in water. To enable the cells to be supplied via the blood, it is bound to lipoproteins for transfer purposes. These can be of different density and are divided based on their centrifugation behavior into chylomicrons, VLDL, IDL, LDL, HDL and lipoprotein a.

Cholesterol is a precursor for steroid hormones and bile acid in the body. It has been found by recent research that cholesterol is used by the body for the biosynthesis of cardiac glycosides.

Using a variety of mechanisms, the body maintains the balance between required and available cholesterol. On the one hand, this is the inhibition of HMG-CoA synthase and reductase, enzymes of cholesterol biosynthesis, and, on the other hand, the metabolization in plasma, the conversion into bile acid and partial excretion with the bile acid and the degradation in plasma. A disturbance of this equilibrium may lead to elevated cholesterol concentrations, which can be determined based on the cholesterol level in the blood. A total cholesterol level in the range of between 190 and 280 mg/dl is considered normal.

The cholesterol status of a person is determined on the basis of the cholesterol value measured in the blood. Based on the latest guidelines for the prevention of cardiovascular diseases, the total cholesterol concentration should be less than 190 mg/dl for healthy people at risk. The recommended maximum LDL values depend on the cardiovascular risk of the respective person. In patients exposed to low to moderate cardiovascular risk, the LDL levels should not exceed is 115 mg/dl, in patients at moderate to high risk the LDL levels should not exceed 100 mg/dl, and in patients with high cardiovascular risk (e.g. known coronary heart disease or diabetes mellitus) the LDL levels should not exceed 70 mg/dl, but the relevant HDL level should be at least 40 mg/dl. High LDL values are considered a risk factor for cardiovascular diseases, while high HDL values are indications of a low risk.

The total cholesterol value usually determines the total value of all cholesterol variants. Moreover, the HDL value is usually determined and the LDL value estimated on the basis of the total cholesterol value, reduced by the value of the HDL cholesterol and 20% of the triglyceride value.

A variety of drugs are employed in the treatment of excessive cholesterol levels, in particular high LDL cholesterol levels. Statins that are capable of intervening in the regulatory cycle are to be mentioned in the first place here. Among the statins, atorvastatin has recently become widely accepted, which is administered in a standard dosage of 10 to 20 mg per day, in cases of severe hypercholesterolemia in an amount of up to 80 mg/day. Same as other statins, atorvastatin has a number of side effects, however, including gastrointestinal disorders, fatigue, muscle pain [statin-associated muscle symptoms (SAMS)], increase in liver enzymes, as well as headaches and joint pain. In addition, there are in rare cases toxic myopathies and an increased risk of diabetes, such risks being classified as serious by the FDA. A problem in this context is that the risks are associated with the dosage to be administered and are already classified as significant at the normal dose.

Moreover, a person's cholesterol levels can be influenced by their diet, in particular by consuming fiber-rich food and yeast products. It is to be noted, however, that this otherwise effective influence is usually not sufficient in the case of very high cholesterol levels.

In the course of metabolization of plant fibers small amounts of propionic acid are produced. As a result of this, propionic acid and its derivatives have been investigated for efficacy in the treatment of hypercholesterolemia. A number of studies were carried out with contradictory results being reported.

Chen et al, Proceedings of the Society for Experimental Biology and Medicine, 175, 215-218 (1984), investigated the effect of the administration of sodium propionate on the cholesterol level of rats with normal and cholesterol-rich diets. In the event propionate was administered to rats consuming cholesterol-rich food, a significant reduction in total cholesterol was detected, while the addition of propionate showed practically no effect in rats that were fed a normal diet. The LDL value was not determined in the study. The sodium propionate dose administered was about 100 mg per day, which in case of humans corresponds to a daily dose of about 30 g.

The authors are aware of the ambivalence of the results obtained; they refer to a study in which pigs were fed comparatively higher doses of propionate and, with reduced total cholesterol, showed a slight increase in the cholesterol content in the liver and a significantly higher cholesterol concentration in back fat.

Berggren et al, British Journal of Nutrition (1996), 76, 287-294, showed that the oral and rectal administration of high doses of sodium propionate to rats did affect liver cholesterol levels only insignificantly. The study makes reference to human studies, according to which the administration of propionate to patients in high doses in one case resulted in a slight reduction of the serum cholesterol level, and in a second case increased the HDL serum cholesterol concentration.

Lin et al, British Journal of Nutrition (1995), 74, 197-207, make mention of major differences in the inhibition of the cholesterol and triacylglycerol synthesis in hepatocytes in humans and rats.

On the whole, it can be concluded that the administration of propionate has an effect on the cholesterol metabolism of a living being, but so far this effect has only been quantified to a limited extent.

It has now been found that a controlled administration of propionate is definitely to suitable to intervene with regulating effect in the cholesterol synthesis and the degradation of cholesterol in a body. In particular, the combination with statins produced positive effects.

In principle, it would be desirable to have available an alternative agent by means of which the cholesterol-lowering effect of statins can be achieved or which, together with statins, results in a noteworthy reduction of the statin dose.

It has been found that propionic acid or its physiologically acceptable derivatives exert a prophylactic or therapeutic effect on high cholesterol levels. They are, in particular, suitable for reducing the LDL serum level to parameters that are acceptable to health.

Propionic acid, $CH_3$—$CH_2$—COOH, is a short-chain fatty acid which is produced in small amounts by the intestinal flora and is generated during the digestion of fiber-rich uncooked vegetarian food. By the food processing industry, it is used as a preservative agent, especially for pasta, and was formerly used extensively for the preservation of bread. However, modern production and packaging methods have meanwhile largely eliminated the need to add preservative agents to bread.

Under propionic acid derivatives primarily their physiologically acceptable salts are to be understood, such as, for example, alkali and alkaline earth salts and in particular sodium, potassium, calcium and magnesium salts. Moreover, salts of other essential metals may also be put to use, for example of iron or zinc, as well as ammonium salt and salts of organic amines. Finally, optional blends of these salts are also considered suitable.

Furthermore, the esters of propionic acid may also be used, in particular esters with lower alcohols, in particular alkyl alcohols with up to 6 carbon atoms. Particularly preferred here are methyl and ethyl esters.

The propionic acid or its derivative is administered at a maximum daily dose of up to 10 g, preferably of up to 5 g. As a rule, amounts ranging between 0.5 g and to 1.5 g per day are sufficient, for example in the form of two administrations of 0.5 g in the morning and evening. A unit dose contains 200 to 1500 mg of active substance, in particular 250 to 1000 mg.

As form of administration capsules or tablets can usually be used. An administration in the form of powder, for example in sachets, is also possible. A capsule, tablet or sachet may contain 0.2 to 1.0 g of active substance, for example 0.5 g of propionic acid salt.

It should be noted that the propionic acid derivatives, after being administered in the body, are predominantly converted into free propionic acid, which takes effect in the intestine.

Capsules, tablets and sachets may contain the active substance together with conventional carriers and auxiliary substances.

Especially preferred is the combination of propionic acid or its derivative with a statin. This combination enables the statin dose to be reduced to half the usual daily dose or less. For said combination, all statins may be used but in particular atorvastatin.

As regards the dosage in combination with atorvastatin, the dosage, for example, is 2×0.5 g propionic acid salt and 5 to 50 mg, preferably 5 to 20 mg and in particular 5 to 10 mg of atorvastatin. As a rule, atorvastatin is administered in doses ranging between 10 and 20 mg or more, depending on the severity of hypercholesterolemia, up to a daily amount of 80 mg. Preferably, the propionic acid derivative is administered in the morning and evening, with atorvastatin being given in the evening, also in the usual way.

For the administration of the combination, it is considered expedient to offer the active ingredients separately in blister packs, with a daily dose comprising of two capsules or tablets of propionic acid salt and one tablet of atorvastatin.

The invention is explained in more detail by way of the enclosed figures, where.

Figure 1:
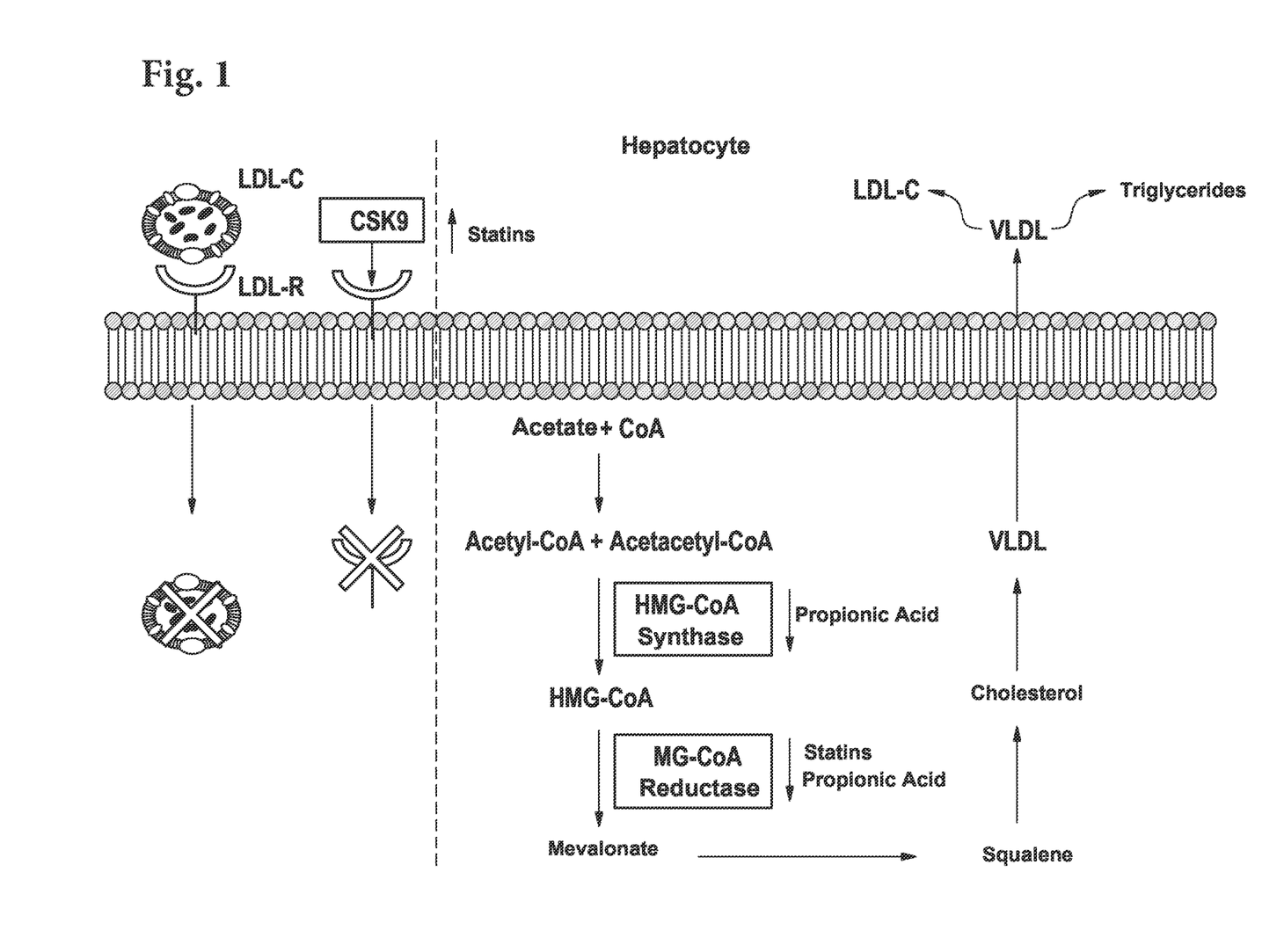
FIG. 1 shows a diagram of cholesterol synthesis/degradation in hepatocytes. The absorption of LDL cholesterol (LDL-C) into hepatocytes with consecutive degradation takes place via LDL receptors (LDL-R) on the cell surface. The degradation of the LDL receptors in turn is promoted, inter alia, by the proprotein convertase subtilisin/kexin type 9 (PCSK9) protease. While the expression of PCSK9 is known to be increased by statins, propionic acid in our experiments has no influence on the PCSK9 expression (see FIG. 7). We demonstrate that the expression of two key enzymes of the cholesterol synthesis is negatively regulated by propionic acid: a) 3-hydroxy-3-methylglutaryl coenzyme A synthase (HMG-CoA synthase) and b) HMG-CoA reductase.

Propionates do not have an effect on the proprotein convertase PCSK9. PCSK9 has clinical significance as it reduces the number of LDL receptors at the cell membrane of liver cells. Via LDL receptors, LDL cholesterol is absorbed into the liver and degraded. (FIG. 1) For that reason, an increased expression of PCSK9 leads to increased concentrations of LDL cholesterol in the blood. One of the major disadvantages of atorvastatin is the increase in PCSK9 expression, which results in a limitation of the cholesterol-lowering effect. This negative effect cannot be detected when using propionates.

Figure 2:
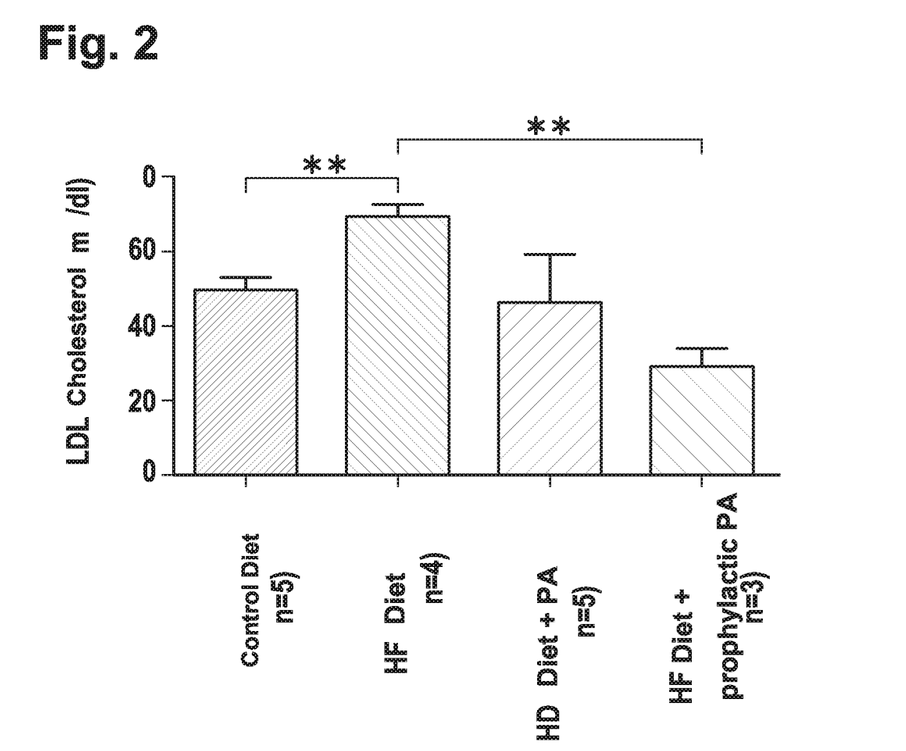
FIG. 2 illustrates the reduction of LDL cholesterol by propionate in the hypercholesterolemic mouse model. HF: High Fat (60 KJ % fat content); PA: Propionic Acid.
Figure 3:
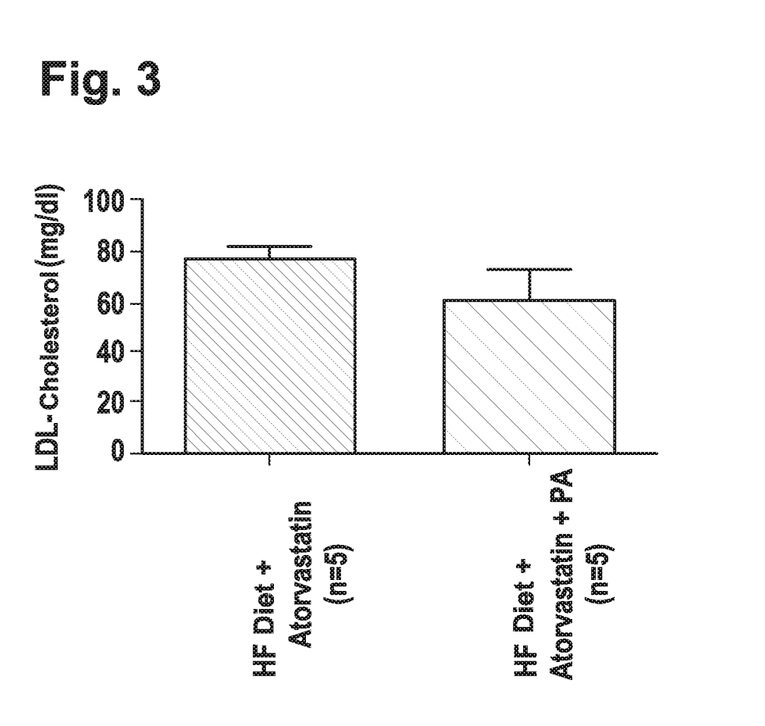
FIG. 3 shows a trend towards further reduction of LDL cholesterol by propionic acid being additionally administered to atorvastatin; HFD: High Fat Diet; PA: Propionic Acid.
Figure 4:
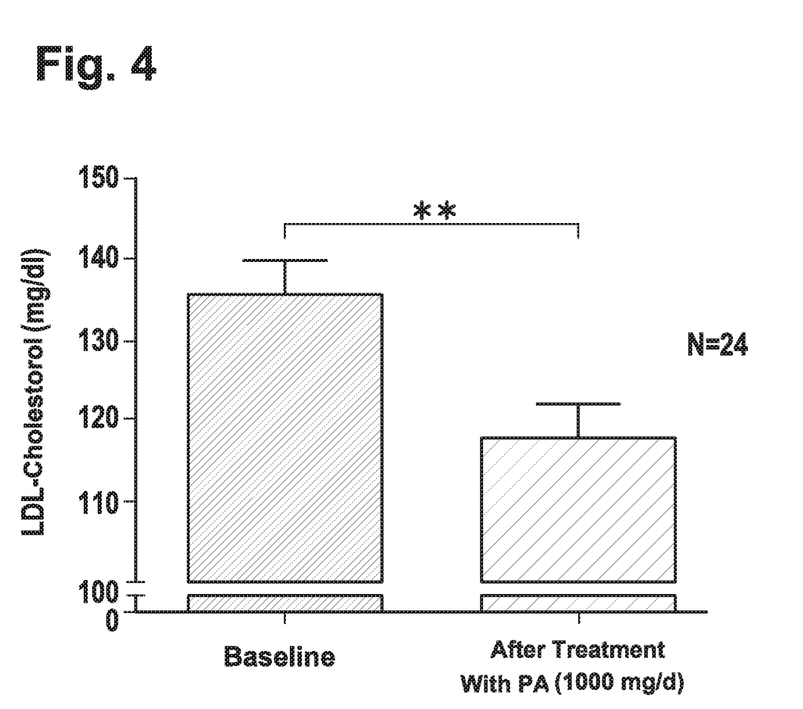
FIG. 4 illustrates the cholesterol-lowering effect of propionic acid in patients with dyslipidemia (n=24, 11 of which male and 13 female participants; between 21-70 years of age) with an initial LDL cholesterol value of >110 mg/dl, after 2-6 months of treatment (n=24).
Figure 7:
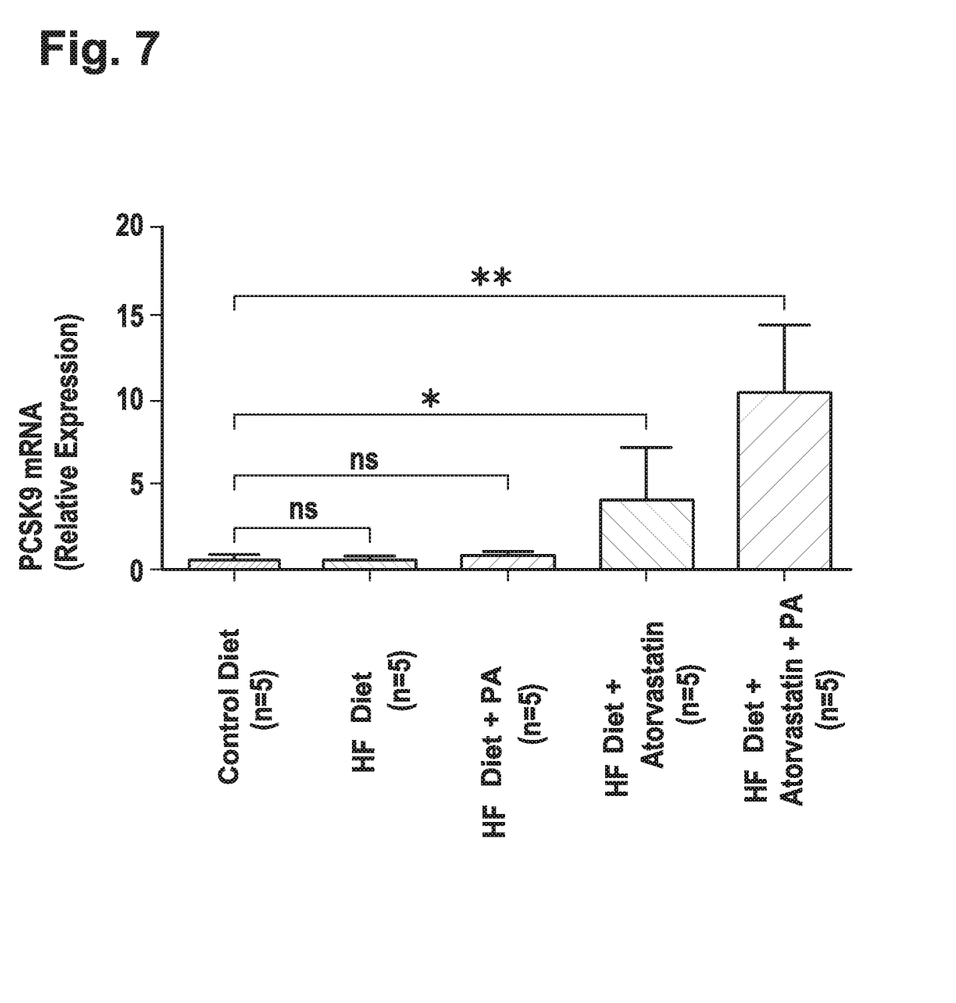
FIG. 7 shows an increased expression of PCSK9 by reverse transcriptase-polymerase chain reaction with atorvastatin being administered. It is to be noted that propionic acid has no influence on PCSK9 expression.
Figure 8:
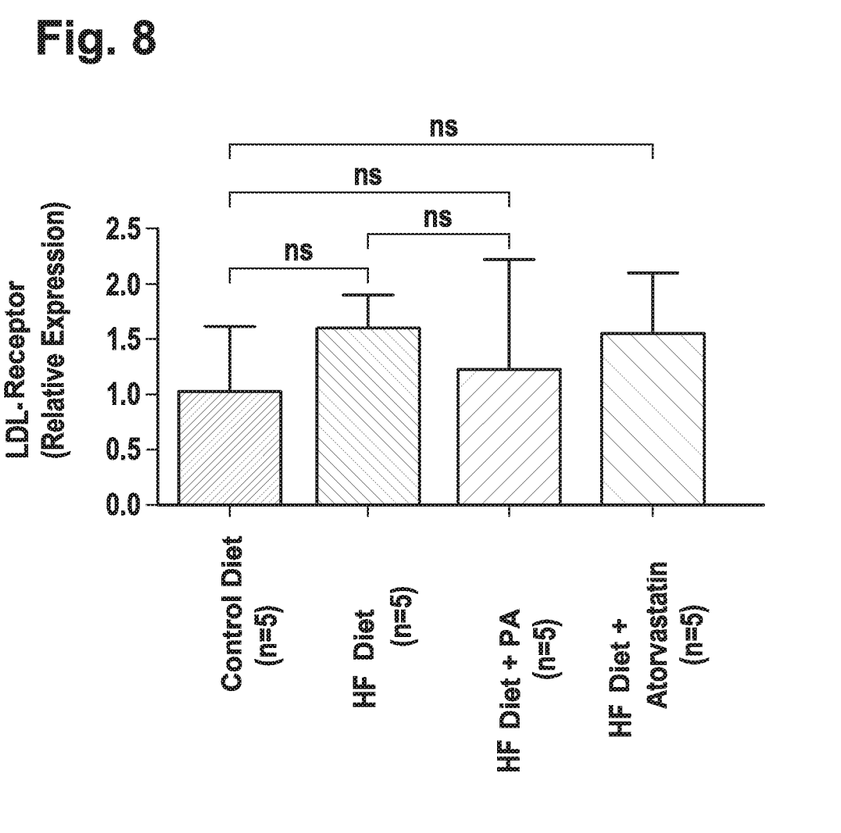
FIG. 8 illustrates the expression of the LDL receptor by reverse transcriptase-polymerase chain reaction in the liver following treatment with propionic acid or atorvastatin. Neither the propionic acid nor the atorvastatin has an effect on the expression of the LDL receptor.
Figure 9:
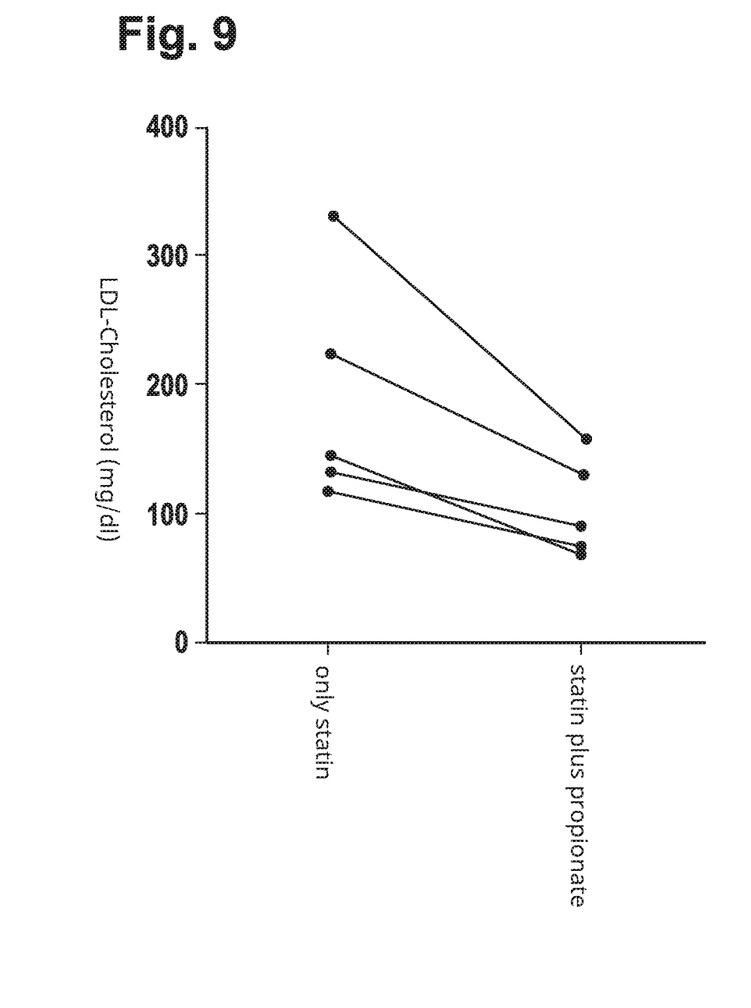
FIG. 9 shows the evaluation of a study carried out on five patients whose LDL cholesterol level had been adjusted to a stable level by administration of atorvastatin. After taking 2×500 mg of propionate for more than eight weeks, the LDL value was reduced as shown in the diagram. The decrease appears to be greatest in patients showing the highest initial LDL value.
Figure 10:
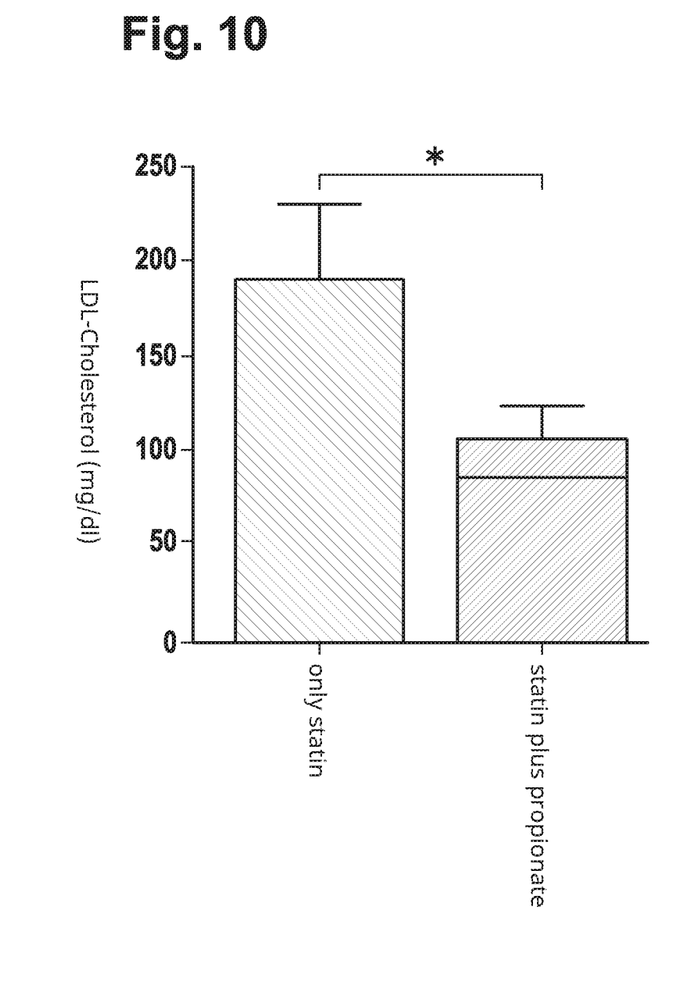
FIG. 10 is a block diagram showing the result of a patient study. On the left, the diagram indicates the averaged initial value of the patients stable through administration of atorvastatin, on the right the averaged LDL value of the patients after taking 2×500 mg of propionate daily for at least eight weeks. This results in a reduction of the LDL value by almost 40% on average.

As can be seen from FIG. 7, the combination of propionate with atorvastatin leads to an even further increase in the expression of PCSK9 compared to atorvastatin alone. However, this does not cause the LDL cholesterol concentration in the blood to be increased, as would be expected, but to a reduction, see FIG. 2.

Figure 5:
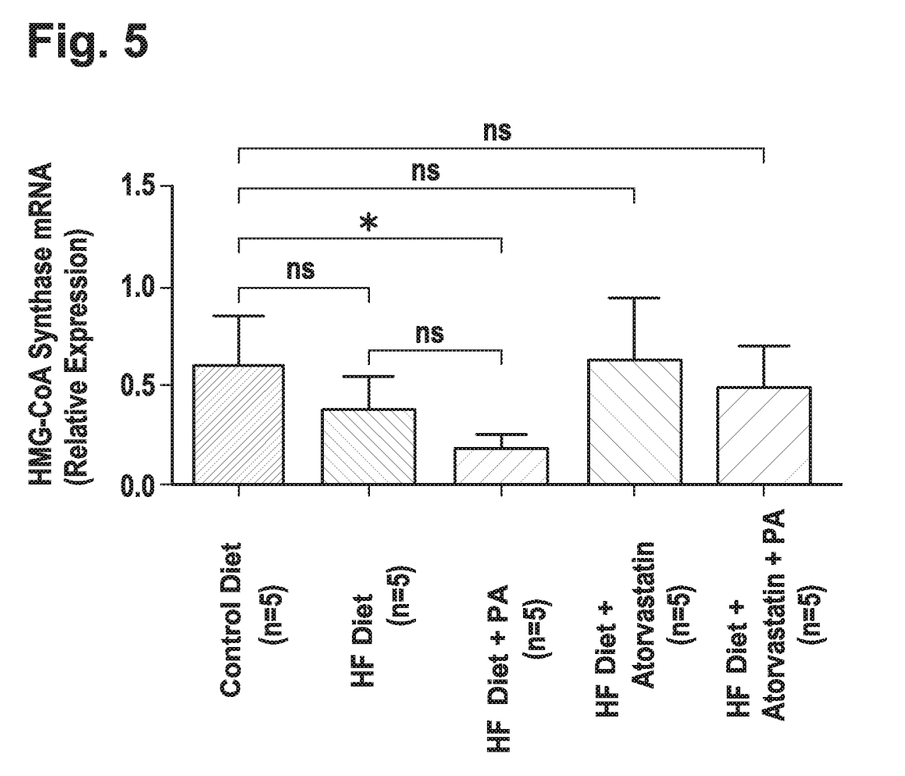
FIG. 5 shows a reduced expression by way of a reverse transcriptase-polymerase chain reaction of HMG-CoA synthase at mRNA level by propionic acid but not by atorvastatin.
Figure 6:
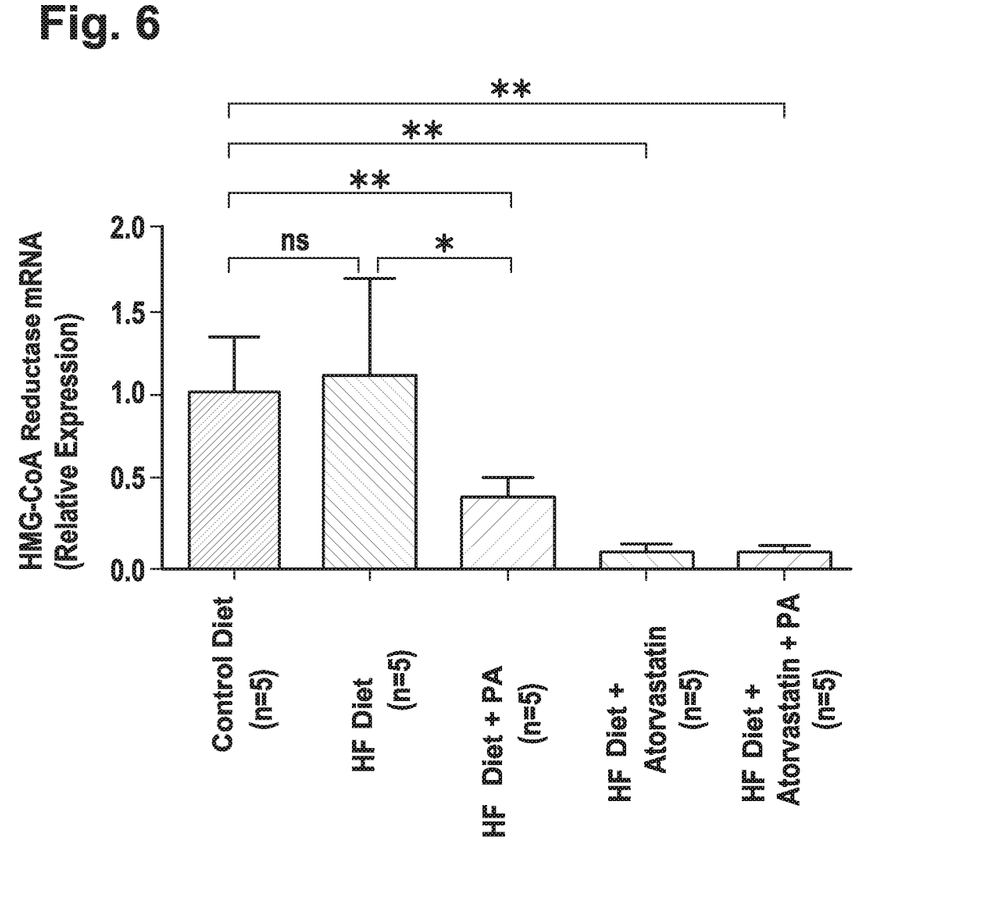
FIG. 6 shows a reduced expression of HMG-CoA reductase by propionic acid by reverse transcriptase-polymerase chain reaction. This effect is also observed when administering atorvastatin.

It can be concluded from FIGS. 5 and 6 that propionates have a massive influence on the expression of HMG-Co-A synthase mRNA and reductase mRNA. Propionate causes both enzymes to be significantly down-regulated, which has a dampening effect on the cholesterol synthesis. With respect to synthase, the effect of propionate is much more pronounced than that of atorvastatin, in reductase atorvastatin has the greater influence.

The patient study attests to the positive influence of 2×500 mg of sodium propionate in addition to atorvastatin. LDL cholesterol levels can be further significantly reduced beyond the stable level achieved with a regular administration of atorvastatin, with the decrease appearing to be greatest when high LDL levels exist.

The invention claimed is:

1. A method for treatment of elevated LDL levels in a human subject in need thereof comprising administering to said human subject a daily dose of about 1 g of propionic acid or a pharmaceutically acceptable salt or ester thereof, wherein the human subject's LDL levels are >100 mg/dL.

2. The method of claim 1, wherein the pharmaceutically acceptable salt or ester thereof is a propionic acid salt.

3. The method of claim 2, wherein the pharmaceutically acceptable salt or ester thereof is an alkali and/or alkaline earth salt of the propionic acid.

4. The method of claim 3, wherein the alkali and/or alkaline earth metal salt of propionic acid is selected from sodium, calcium, and/or magnesium propionate.

5. The method of claim 1, wherein the daily dose is administered in the form of one or more tablets, capsules, or sachets.

6. The method of claim 1 wherein the daily dose further comprises a pharmaceutically acceptable carrier and/or excipient.

7. The method of claim 1 further comprising co-administering daily a statin drug.

8. The method of claim 7, wherein the statin drug is atorvastatin.

9. The method of claim 8, wherein the daily dose of atorvastatin is between about 5 to about 50 mg.

10. The method of claim 9, wherein the daily dose of atorvastatin is between about 5 mg to about 20 mg.

11. The method of claim 10, wherein the daily dose of atorvastatin is between about 5 mg to about 10 mg.

12. The method of claim 7, wherein the daily dose of propionic acid is in the form a calcium and/or magnesium salt and the daily dose of the statin drug are separately provided in a blister pack.

13. The method of claim 12, wherein the blister pack contains two about 0.5 g unit doses of calcium and/or magnesium propionate and one about 5 mg unit dose of atorvastatin.

14. A method of treating elevated LDL levels in a human subject in need thereof comprising administering to said human subject a daily dose of about 1 g of a calcium and/or magnesium propionic acid salt and a daily dose of a statin drug, wherein the human subject's LDL levels are >100 mg/dL.

15. The method of claim 14, wherein the statin is atorvastatin and the calcium and/or magnesium propionic acid salt and atorvastatin are kept separate in a blister pack wherein the blister pack contains two about 0.5 g unit doses of the calcium and/or magnesium propionic acid salt and one about 5 mg unit dose of atorvastatin.

16. The method of claim 14, wherein daily dose of the about 1 g of propionic acid or a pharmaceutically acceptable salt or ester thereof is administered in about 0.5 g unit doses twice a day.

17. The method of claim 1, wherein daily dose of the about 1 g of propionic acid or a pharmaceutically acceptable salt or ester thereof is administered in about 0.5 g unit doses twice a day.

18. A method for treatment of elevated LDL levels in a human subject in need thereof comprising administering to said human subject a therapeutic agent consisting essentially of propionic acid or a pharmaceutically acceptable salt or ester thereof.

19. The method of claim 18 comprising about 1 g of a calcium and/or magnesium propionic acid salt.

20. The method of claim 18, wherein the elevated LDL levels are >110 mg/dL.

21. The method of claim 19, wherein the about 1 g of the calcium and/or magnesium propionic acid salt is administered in about 0.5 g doses twice a day.

22. A method of treatment of elevated LDL levels in a human subject in need thereof comprising administering to said human subject a first therapeutic agent consisting essentially of propionic acid or a pharmaceutically acceptable salt or ester thereof and a second therapeutic agent consisting essentially of a statin drug.

23. The method of claim 22, wherein propionic acid or pharmaceutically acceptable salt or ester thereof is a calcium and/or magnesium propionic acid salt and the statin drug is atorvastatin, wherein the calcium and/or magnesium propionic acid salt and atorvastatin are kept separate in a blister pack, wherein the blister pack contains two about 0.5 g unit doses of the calcium and/or magnesium propionic acid salt and one about 5 mg unit dose of atorvastatin.

24. The method of claim 23, wherein the about two about 0.5 g unit doses of a calcium and/or magnesium propionic acid salt are administered separately twice a day.

25. The method of claim 23, wherein the unit doses of calcium and/or magnesium propionic acid salt are in the form of a tablet, capsule, or sachet.

26. The method of claim 22, wherein the elevated LDL levels are greater than 110 mg/dL.

27. A method for treatment of elevated LDL levels in a human subject in need thereof comprising administering to said subject twice a day an about 0.5 g unit dose of calcium and/or magnesium propionic acid in combination with a daily unit dose of atorvastatin, wherein the human subject's LDL levels are >100 mg/dL.

28. A method of claim 27, wherein the calcium and/or magnesium propionic acid salt and atorvastatin are kept separate in a blister pack, wherein the blister pack contains two about 0.5 g unit doses of the calcium and/or magnesium propionic acid salt and one about 5 mg unit dose of atorvastatin.

* * * * *